(12) United States Patent
Lucchino

(10) Patent No.: US 8,473,315 B1
(45) Date of Patent: Jun. 25, 2013

(54) DETECTION OF ADVERSE REACTIONS TO MEDICATION USING A COMMUNICATIONS NETWORK

(76) Inventor: Ronald Lucchino, Long Boat Key, FL (US)

(*) Notice: Subject to any disclaimer, the term of this patent is extended or adjusted under 35 U.S.C. 154(b) by 0 days.

(21) Appl. No.: 13/588,375

(22) Filed: Aug. 17, 2012

(51) Int. Cl.
*G06F 19/00* (2011.01)

(52) U.S. Cl.
USPC .............................................. 705/3

(58) Field of Classification Search
USPC .............................................. 705/3
See application file for complete search history.

(56) References Cited

U.S. PATENT DOCUMENTS

| | | | |
|---|---|---|---|
| 6,000,828 | A | 12/1999 | Leet |
| 6,789,091 | B2 | 9/2004 | Gogolak |
| 7,461,006 | B2 | 12/2008 | Gogolak |
| 7,542,961 | B2 | 6/2009 | Gogolak |
| 7,596,503 | B2 | 9/2009 | Ben-Attar |
| 7,653,639 | B2 | 1/2010 | Classen |
| 7,979,373 | B2 | 7/2011 | Gogolak |
| 2002/0095261 | A1 | 7/2002 | Gut |
| 2004/0202571 | A1 | 10/2004 | Epler |
| 2006/0195041 | A1 | 8/2006 | Lynn |
| 2008/0082361 | A1 | 4/2008 | Marge |
| 2009/0055378 | A1 | 2/2009 | Alecu |
| 2009/0158211 | A1 | 6/2009 | Gogolak |
| 2010/0070304 | A1* | 3/2010 | Levinson .................. 705/3 |
| 2010/0129831 | A1 | 5/2010 | Brenner |
| 2010/0191073 | A1 | 7/2010 | Tarassenko |
| 2011/0258231 | A1 | 10/2011 | Cao |

OTHER PUBLICATIONS

FDA website (http://www.fdable.com/advanced_aers_query/).*

* cited by examiner

*Primary Examiner* — John Pauls
(74) *Attorney, Agent, or Firm* — Mark Terry

(57) ABSTRACT

A method for detecting an adverse drug event in a patient. The method includes reading an adverse drug reaction (ADR) description of the patient, reading identifiers for medications currently taken by the patient, and accessing ADR records corresponding to the identifiers. Each record comprises an identifier for a medication, an ADR description for the medication and a risk profile for the medication. Next, the method compares the ADR description of the patient with ADR descriptions in the ADR records, identifies an ADR record with a matching ADR description and calculates a level of risk that a medication of the ADR record is causing the ADR description of the patient. Finally, the method transmits an identifier and a risk profile for each medication of the ADR record, and a notice indicating that each medication of the ADR record may be causing the ADR description of the patient.

5 Claims, 6 Drawing Sheets

DETECTION OF ADVERSE REACTIONS TO MEDICATION USING A COMMUNICATIONS NETWORK

CROSS-REFERENCE TO RELATED APPLICATIONS

This patent application claims priority to utility patent application Ser. No. 13/526,490 filed Jun. 18, 2012 and entitled "Detection of Adverse Reactions to Medications," which claims priority to provisional patent application No. 61/498,258 filed Jun. 17, 2011 and entitled "Detection of Adverse Reactions to Medication." The subject matter of patent application Ser. No. 13/526,490 and patent application No. 61/498,258 is hereby incorporated by reference in their entirety.

STATEMENT REGARDING FEDERALLY SPONSORED RESEARCH OR DEVELOPMENT

Not Applicable.

INCORPORATION BY REFERENCE OF MATERIAL SUBMITTED ON A COMPACT DISC

Not Applicable.

FIELD OF THE INVENTION

The invention disclosed broadly relates to the field of medicine, and more particularly relates to the field of medications and pharmaceuticals.

BACKGROUND OF THE INVENTION

Prescribed medications can, in certain situations, cause adverse drug reactions in patients. Less drastic adverse drug reactions, such as change in mood, loss of appetite, and nausea, may diminish the quality of life. But although some adverse drug reactions are not very serious, others cause death, hospitalization, or serious injury. In the United States, more than 2 million people each year are injured by adverse drug reactions, including more than 100,000 fatalities. When considered as a fraction of all mortalities, adverse drug reactions are one of the leading causes of death in the United States. In many cases, adverse drug events could and should have been avoided.

More adverse reactions occur in patients 60 or older. There are various reasons for the propensity of older patients to experience adverse drug reactions, including smaller bodies, different body composition, decreased ability of the liver and/or kidney to process drugs, increased drug sensitivity, decreased blood pressure maintaining ability, additional medications and inadequate testing of drugs on older adults. Consequently, older patients require more thorough medical care when exposed to a drug treatment.

Physicians and healthcare workers must evaluate whether a prescribed medication is causing an adverse reaction in the patient before the medication is deemed safe for the patient. One approach to this problem involves a distributed and network-accessible database that logs and disseminates information pertaining to adverse drug reactions (ADRs) among pharmaceutical providers, such as pharmacies. These Pharmacy Managed Systems (PMS) provide for the storage and distribution of data pertaining to treatment and monitoring of ADRs. This approach, however, leaves much to be desired. One problem with this approach is that no patient orientation is provided. Without appropriate interaction and information from the patient, the ability of a PMS to detect an ADR is decreased. Further, the current approach does not match an ADR with the observed changes in an older patient. A conventional PMS simply lists common ADRs for given medications, and the healthcare worker must match the listed information to the ADR being experienced by the patient. Additionally, the current approach does not identify multiple medications with similar ADRs that may be mimicking the observed changes in a patient. This identification process is left to the health care professional who must review all medications and their associated ADRs in order to determine which ADR may match the observed changes. This approach is time consuming, resulting in very few patient reviews being made, and is at a high risk for errors. Consequently, the current approach algorithm is only effective in residential care settings, rather than community settings.

Therefore, a need exists to overcome the problems with the prior art as discussed above, and particularly for a more efficient way of detecting adverse reactions to medication.

SUMMARY OF THE INVENTION

Briefly, according to an embodiment of the present invention, a method for detecting an adverse drug event in a patient via the use of a communications network is disclosed. The method includes receiving from a user, via the communications network, at least one adverse drug reaction (ADR) description corresponding to the patient, receiving from a user, via the communications network, one or more identifiers for medications that are currently taken by the patient, accessing one or more ADR records corresponding to the one or more identifiers for medications that are currently taken by the patient, wherein each record comprises an identifier for a medication, one or more ADR descriptions for the medication and a risk profile for the medication, comparing the at least one ADR description corresponding to the patient with ADR descriptions in the one or more ADR records that were accessed, identifying at least one ADR record, of the one or more ADR records that were accessed, which includes an ADR description matching the ADR description corresponding to the patient, calculating a level of risk that at least one medication of the at least one ADR record is causing the ADR description corresponding to the patient, wherein the level of risk is calculated based on the risk profile in the at least one ADR record, and transmitting to the user, via the communications network, an identifier and a risk profile for each medication of the at least one ADR record, and a notice indicating that each medication of the at least one ADR record may be causing the ADR description corresponding to the patient.

The foregoing and other features and advantages of the present invention will be apparent from the following more particular description of the preferred embodiments of the invention, as illustrated in the accompanying drawings.

BRIEF DESCRIPTION OF THE DRAWINGS

The subject matter, which is regarded as the invention, is particularly pointed out and distinctly claimed in the claims at the conclusion of the specification. The foregoing and other features and also the advantages of the invention will be apparent from the following detailed description taken in conjunction with the accompanying drawings.

DETAILED DESCRIPTION

The present invention provides a quick, user-friendly and automated method for aiding in the early detection of ADR, as well as a centralized repository for collecting and disseminating ADR data to healthcare providers and patients. The present invention improves over the prior art by providing an ADR detection system that, due to its expediency, may be used in various point-of-care situations, such as community settings, as well as hospital and clinic settings. This results in an ADR detection system that is particularly well-suited for use with elderly patients, whom are at the highest risk for ADR. Further, the present invention facilitates interaction with patients, which increases the ability of the system to detect an ADR. Further, the present invention matches an observed ADR in a patient with common ADRs for the medications taken by that patient, which uniquely addresses issues commonly experienced with older patients. Additionally, the present invention identifies multiple medications with similar ADRs that may be mimicking the observed changes in a patient. Finally, when dealing with multiple medications with similar ADRs, the present invention allows for the calculation of risk data associated with each of the multiple medications, thereby allowing a healthcare provider to evaluate all potential ADR candidates at once.

Figure 1:
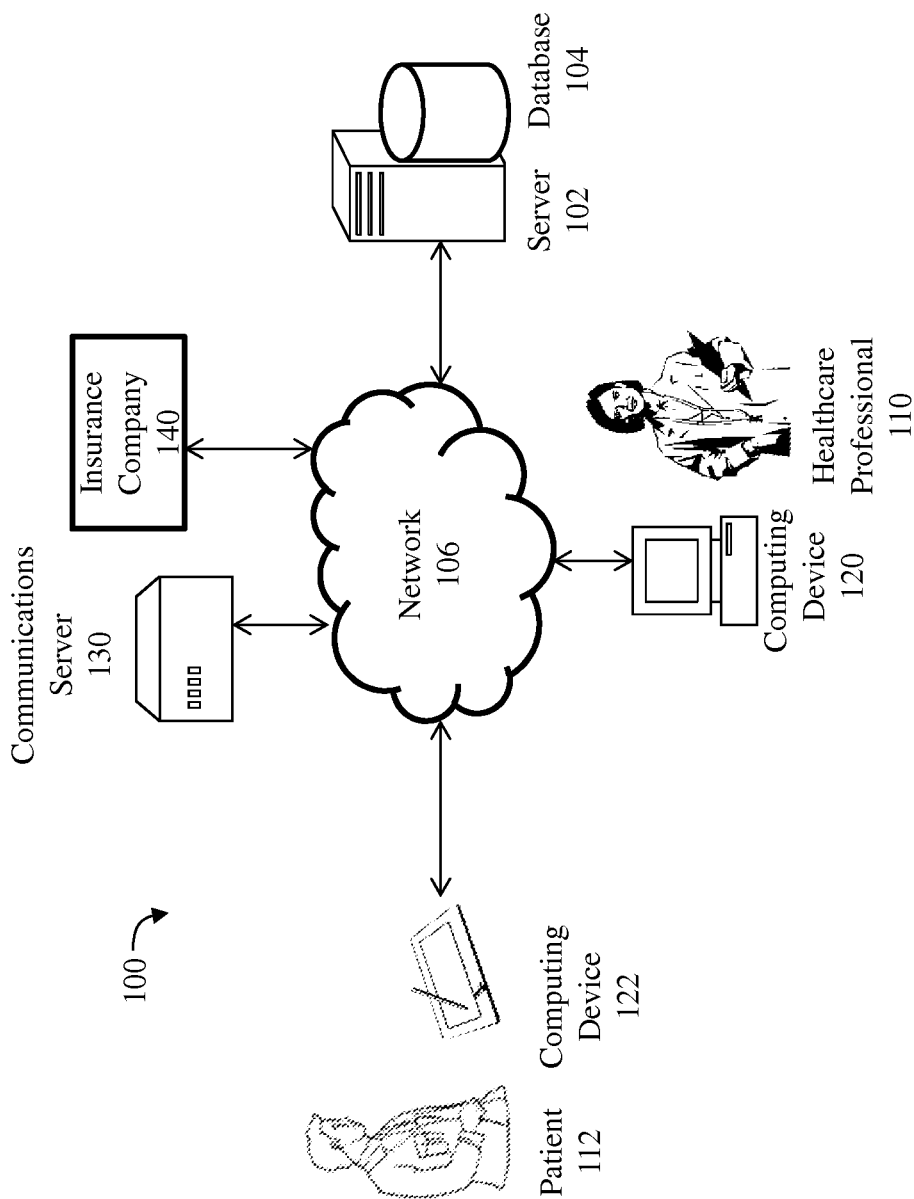
FIG. 1 is an illustration of a block diagram showing the network architecture of a system for providing detection of FIG. 1 is a block diagram of an operating environment that supports a process for detection of ADR and storage and dissemination of related data via a server communicatively coupled with a communications network, according to an example embodiment.

Referring now to the drawing figures in which like reference designators refer to like elements, there is shown in FIG. 1 is a block diagram of an operating environment 100 that supports a process for detection of ADR and storage and dissemination of related data via a server 102 communicatively coupled with a communications network 106, according to an example embodiment. The environment 100 may comprise at least two computing devices 120, 122 and a server 102 communicating via a communications network 106. The computing devices 120, 122 may be connected either wirelessly or in a wired or fiber optic form to the communications network 106. Further, environment 100 includes communications server 130 coupled to network 106. Communications network 106 may be a packet switched network, such as the Internet, or any local area network, wide area network, enterprise private network, cellular network, phone network, mobile communications network, or any combination of the above.

Server 102 and computing devices 120, 122 may each comprise a computing device 600, described below in greater detail with respect to FIG. 6. Further, server 102 and computing devices 120, 122 may each comprise mobile computing devices such as cellular telephones, smart phones, tablet computers, or other computing devices such as a desktop computer, laptop, game console, etc.

Server 102 includes a software engine that delivers applications, data, program code and other information to networked devices 120, 122 and 130. Namely, server 102 performs the processing, storage and dissemination of ADR data, all of which are provided to the entities 120, 122 and 130, wherein the provision of the foregoing services and data facilitates the detection of ADR. The software engine of server 102 may perform other processes such as transferring multimedia data, such as audio and video, in a stream of packets that are interpreted and rendered by a software application as the packets arrive. It should be noted that although FIG. 1 shows only two computing devices 120, 122, the system of the present invention supports any number of computing devices connected via network 106.

Server 102, and computing devices 120, 122 may each include program logic comprising computer source code, scripting language code or interpreted language code that perform various functions of the present invention. In one embodiment, the aforementioned program logic may comprise program module 607 in FIG. 6.

FIG. 1 further shows that server 102 includes a database or repository 104, which may be a relational database comprising a Structured Query Language (SQL) database stored in a SQL server. Computing devices 120, 122 may also each include databases. The database 104 may serve data used by server 102, computing devices 120, 122, server 130 and insurance company 140 during the course of operation of the invention.

Environment 100 may be used when computing devices 120, 122, as well as entities 130, 140, transfer data to and from database 104 coupled to server 102. Various types of data may be stored in the database 104 of server 102. For example, the database 104 may store one or more medication records for each medication. A medication record, also known as an ADR record 220, may comprise information about a medication, such as a unique identifier, a name, a chemical formula, dosage information, etc. An ADR record may also include ADR data, such as a description of one or more common ADRs associated with the medication (also known as an ADR description), remedies for common ADRs and related data. Lastly, an ADR record may include a risk profile that may comprise a numerical or textual probability that a particular ADR is caused by the medication. If an ADR record lists more than one ADR, there may be a risk profile defined for each ADR of a particular medication. Lastly, an ADR record may include a link or other pointer to a patient record.

In one embodiment, a risk profile may be a numerical probability, such as 50%, or may be a textual probability, such as unlikely, likely, highly likely, mild, minor, moderate, severe, etc. In another embodiment, a risk profile can be a numerical or textual indicator that represents either; a) acceptable risk (i.e., the particular medication poses an acceptable risk—e.g., not life threatening—in causing a particular ADR) or b) high risk (i.e., the particular medication poses a high risk—e.g., life threatening—in causing a particular ADR). In yet another embodiment, even though a particular ADR may have a risk profile indicating acceptable risk in relation to one medication, if a particular patient is taking multiple medications and several of those medications list the same ADR, the risk profile calculated for the patient (such as in step 410 or FIG. 5 below) may result in a risk profile of high risk. Thus, if multiple medications taken by a particular patient, such as three or more medications, have the same or similar ADR, then the server 102 will assign the particular ADR a risk profile indicating high risk.

In yet another embodiment, a risk profile may have more than one portion. A first portion of the risk profile may be a numerical or textual indicator that represents either acceptable risk or high risk, as defined above. A second portion of the risk profile may be a numerical or textual indicator that represents either acceptable risk or high risk, in relation to people of advanced age, i.e., the elderly. An example of a medication with a high risk of causing one or more ADRs is a medication with substantial anticholinergic properties.

In one alternative, an ADR record may comprise a record that includes an ADR description, a list of one or more medications that may cause the ADR, and information about each medication, such as a unique identifier, a name, a chemical formula, dosage information, etc. An ADR record may also include remedies for the ADR and a risk profile for each medication listed. Lastly, an ADR record may include a link or other pointer to a record for a medication.

The database 104 may also store one or more synonym records 225 for each ADR of an ADR record 220. A synonym record may include one or more alphanumeric words or phrases that serve as synonyms for a particular ADR description of an ADR record 220. A synonym record may also include a pointer to an ADR record 220 or any of the information located in an ADR record. Take, for example, the ADR description "stomach pains." A synonym record for the example ADR description may include the alphanumeric text "indigestion," "nausea," or "abdominal pain." A synonym record is used during the process of matching a patient's ADR description with the ADR descriptions found with the medications the patient is taking, described more fully below with reference to step 408.

The database 104 may also store one or more patient records for each patient, i.e., a patient record. A patient record may include personal data for the patient 112, which may include contact information for a patient 112, a medical history of the patient, a list of medications (past and current) taken by patient, start and stop dates for each medication taken by patient, a list of ADRs experienced by the patient, start and stop date for ADRs experienced by the patient, clinical data of the patient, psychological data of the patient, occupational data of the patient, etc. A patient record may also include risk data based on the personal data for the patient 112, wherein the risk data defines the patient's risk of developing a current medical affliction or having a recurrence of a current affliction. Advanced age, for example, may be a cause for assigning a high risk category to the risk data of a patient record. Lastly, a patient record may include a link or other pointer to an ADR record.

Additionally, a patient record may also include one or more medication regimens for a patient, which have been assigned or prescribed by a healthcare professional 110, such as a doctor, nurse, pharmacist or physician's assistant. A drug regimen includes an identifier for one or more medications, a number of pills or days the patient must take the medications and the number of pills the patient must take each day or week. Moreover, a patient record may also include compliance data, wherein the compliance data defines the patient's level of compliance with the medication regimen. In one embodiment, any of the data elements described above for ADR records or patient records may be stored in a record in alphanumeric format or simply numeric format.

Note that although server 102 is shown as a single and independent entity, in one embodiment of the present invention, the functions of server 102 may be integrated with another entity, such as the computing device 120 and the server 130. Further, server 102 and its functionality, according to a preferred embodiment of the present invention, can be realized in a centralized fashion in one computer system or in a distributed fashion wherein different elements are spread across several interconnected computer systems.

FIG. 1 further shows communications server 130 communicatively coupled with the network 106. The communications server 130 comprises a server having functionality for making telephone calls to the healthcare professional 110, or any other individual, in either an automated fashion using an interactive voice response system or via a live operator. The communications server 130 may further comprise a server having email, text and other instant messaging capabilities. FIG. 1 also shows insurance company 140, which may comprise an insurer that provides health related insurance policies covering the cost of medical treatments for patients.

Figure 3:
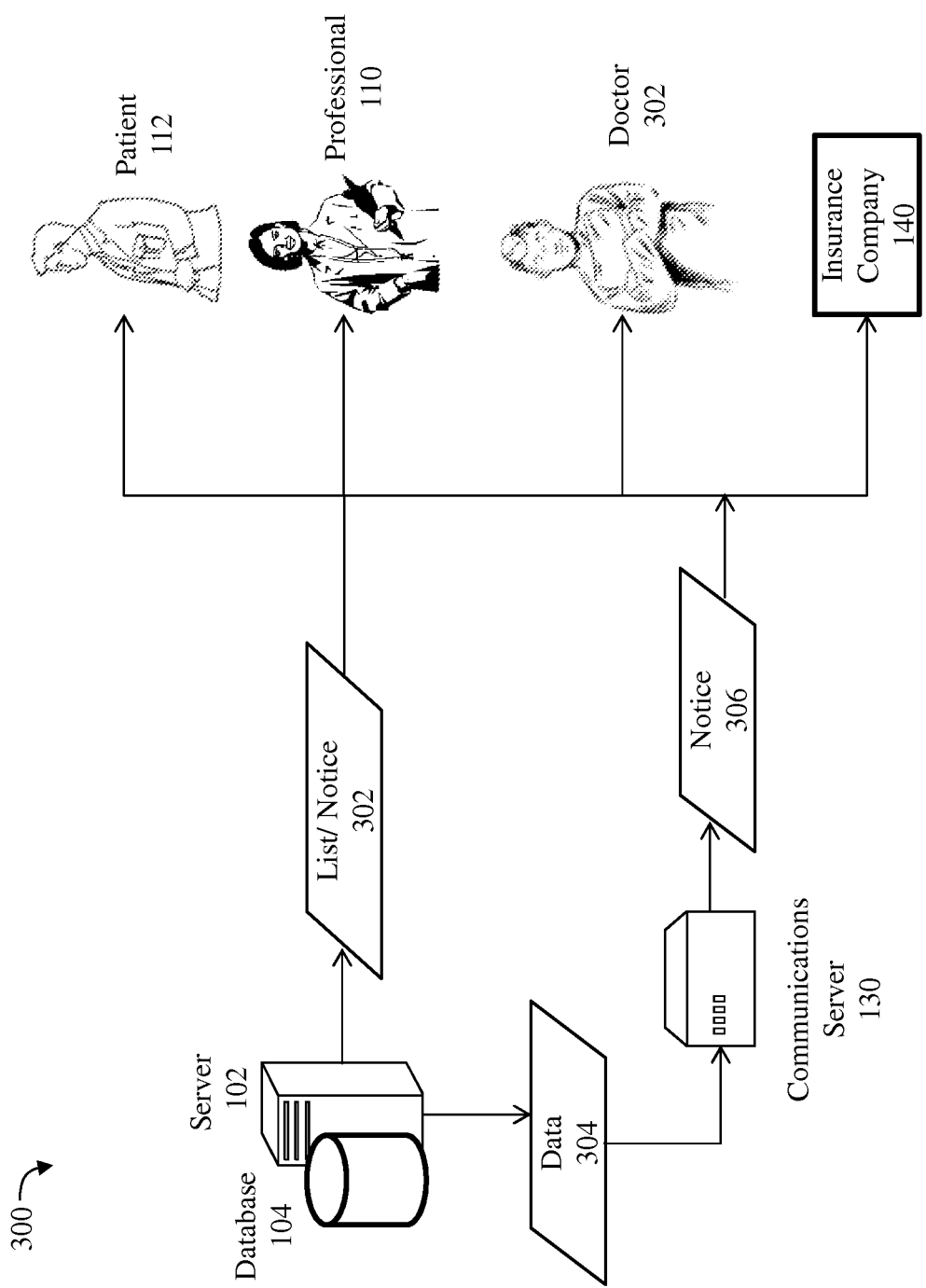
FIG. 3 is a diagram showing an additional data flow of the process for detection of ADR and storage and dissemination of related data, according to an example embodiment.
Figure 4:
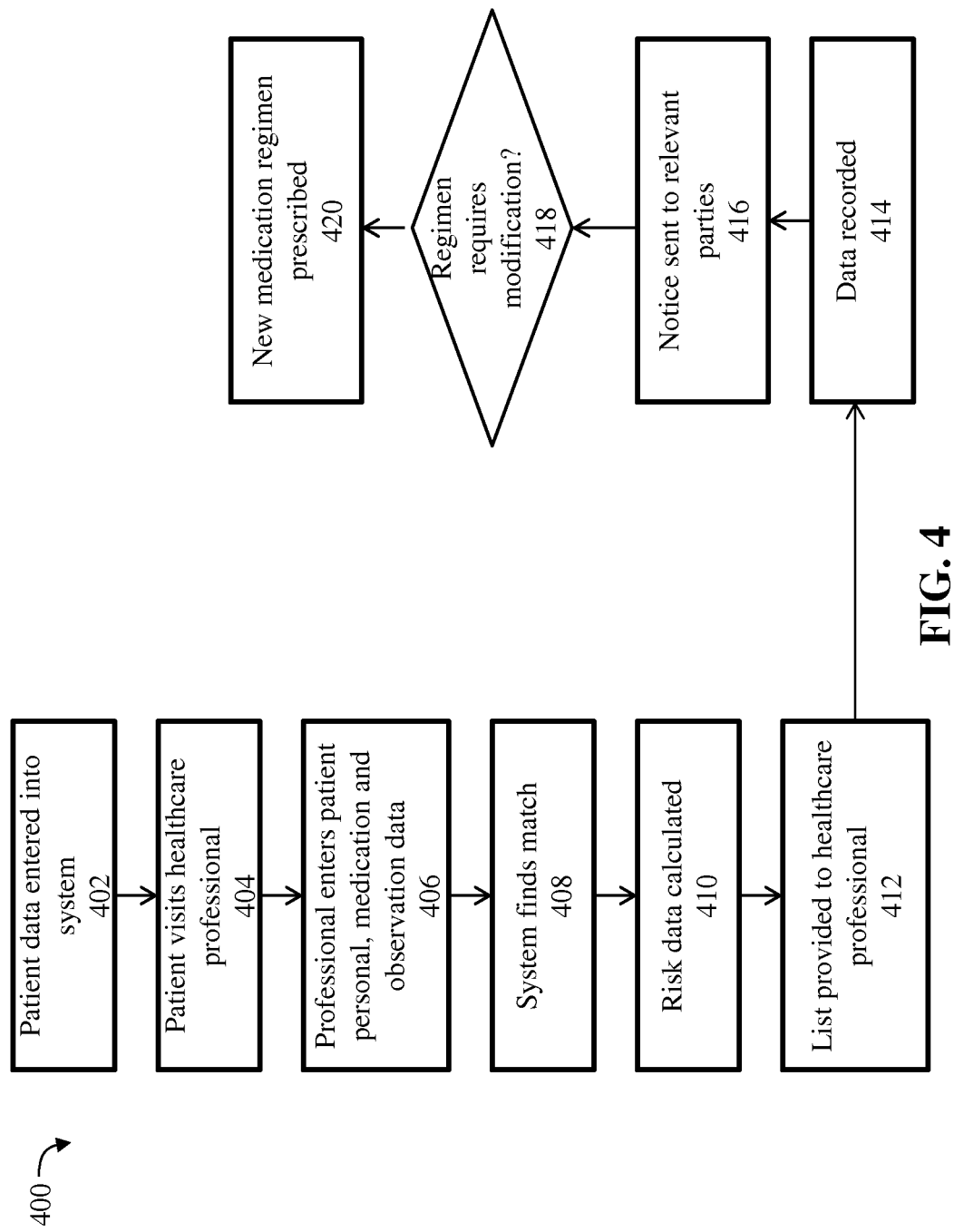
FIG. 4 is a flow chart of a method for facilitating detection of ADR and storage and dissemination of related data via a server communicatively coupled with a communications network, according to an example embodiment.

The process of the present invention will now be described with reference to FIG. 1 above. FIG. 4 is a flow chart of a method 400 for facilitating detection of ADR and storage and dissemination of related data via the server 102 communicatively coupled with a communications network 106, according to an example embodiment. The method 400 of FIG. 4 will be described with reference to FIG. 2 and FIG. 3, which visually depict the data flow of the process for detection of ADR and storage and dissemination of related data. As a preliminary matter, the database 104 has previously been populated with ADR records. Method 400 begins with stage 402.

In stage 402, patient data is entered into a patient record in the database 104. This may be accomplished by patient 112 interacting with a computing device 122 or may be accomplished by a healthcare professional 110, or her agent or employee, interacting with device 120. Next, in stage 404, the patient 112 visits the healthcare professional 110 because he may be experiencing an ADR.

In stage 406, the healthcare professional 110 executes an application on device 120 that displays a graphical user interface communicatively coupled with server 102 via network 106. The professional 110 proceeds to enter personal data 202 about patient 112 into the interface, such as name, age, sex, location, social security number, etc. In one alternative, the professional 110 accesses a patient record in database 104 using the personal data 202. Also in stage 406, the professional 110 proceeds to enter observation data 204 about patient 112 into the interface, such as a textual description of the symptoms being experienced by the patient 112, also known as an ADR description. Further in stage 406, the professional 110 proceeds to enter medication data 206 about patient 112 into the interface, such as a textual description of the medications currently being taken by the patient 112, when he or she started taking the medication, etc.

In one embodiment of the present invention, the data 202, 204, 206 entered via interface in stage 406 may be entered via the use of pull down menus or searchable lists wherein predefined lists of data are provided in a logical order within a common graphical user interface widget for selection by the user.

In stage 408, the server 102 accesses from database 104 a first set of ADR records associated with the medications defined in data 206 and proceeds to attempts to find a match between the ADR description in data 204 and the ADR descriptions in the first set of ADR records. In one embodiment, the server 102 compares alphanumeric text of the ADR description in data 204 with alphanumeric text of ADR descriptions in the first set of ADR records. Any ADR records in the first set of ADR records that contain a match are deemed matched ADR records.

In another embodiment, in step 408, the server 102 accesses from database 104 a set of synonym records associated with the medications defined in data 206 and proceeds to attempts to find a match between the ADR description in data 204 and the ADR descriptions in the set of synonym records. The server 102 compares alphanumeric text of the ADR description in data 204 with alphanumeric text in synonym records 225 in database 104. Recall that a synonym record may include one or more alphanumeric words or phrases that serve as synonyms for a particular ADR description of an ADR record 220. If the server 102 finds a match between the ADR description in data 204 and alphanumeric text in a synonym record 225, then the server 102 recognizes a match between the ADR description in data 204 and the ADR record 220 associated with the synonym record 225. Via the aforementioned matching process, any ADR records in the first set of ADR records that contain a match are deemed matched ADR records.

In stage 410, the server 102 calculates risk data for each of the matched ADR records. Specifically, the server 102 calculates a level of risk that the medication of each matched ADR record is causing the ADR description in data 204, wherein the level of risk is calculated based on the risk profile in the matched ADR record. In one embodiment, the calculation of step 410 further comprises reading the age of the patient from the patient record or from data 202 in order to determine the level of risk the ADR poses to a person of advanced age. The calculations of step 410 are described in greater detail below.

In step 412, the server 102 prepares a list 410 that describes each medication in each matched ADR record, and level of risk that the medication of each matched ADR record is causing the ADR description in data 204, as calculated in step 410. Note that in an embodiment where a risk profile comprises two portions, the list 410 may comprise two risk levels for each ADR. For example, for one particular ADR, the list 410 may state: "acceptable risk, high risk for elderly patients," which indicates that the medication may be an acceptable risk for most patients for the particular ADR, but a high risk for patients of advanced age.

In step 412, the server 102 also prepares a notice indicating that each medication of each matched ADR record may be causing the ADR description in data 204. Further in step 412, the aforementioned items prepared by server 102 are transmitted to device 120 via network 106 for display in the graphical user interface executing in the device 120. The professional 110 may then view the list 210 and notice and decide how to treat the patient 112.

In step 414, any of the data 202, 204, 206 entered via interface in stage 406, as well as the risk data generated in step 410, may be stored in conjunction with a patient record of the patient 112 in database 104. Further, any of the data 202, 204, 206 entered via interface in stage 406, as well as the risk data generated in step 410, may be stored in conjunction with each matched ADR record in database 104.

In step 416, the server 102 transmits a notice 302 to one or more relevant parties such as through email, text message, automated, phone call, etc. For example, server 102 may send a notice 302 to one or more of the patient 112, the professional 110 or another healthcare professional, such as a doctor 302, charged with treating the patient 112. In another example, the server 102 may send the notice 302 to the insurance company 140 so as to inform them as to the ADR experienced by the patient 112. The insurance company 140 may seek to utilize the ADR data to alert other healthcare providers and proscribe best practices in the medical field with regard to the medications that may have caused the ADR. The data provided in the notice 302 may include any of the data in the list 210 and notice of FIG. 2.

Figure 2:
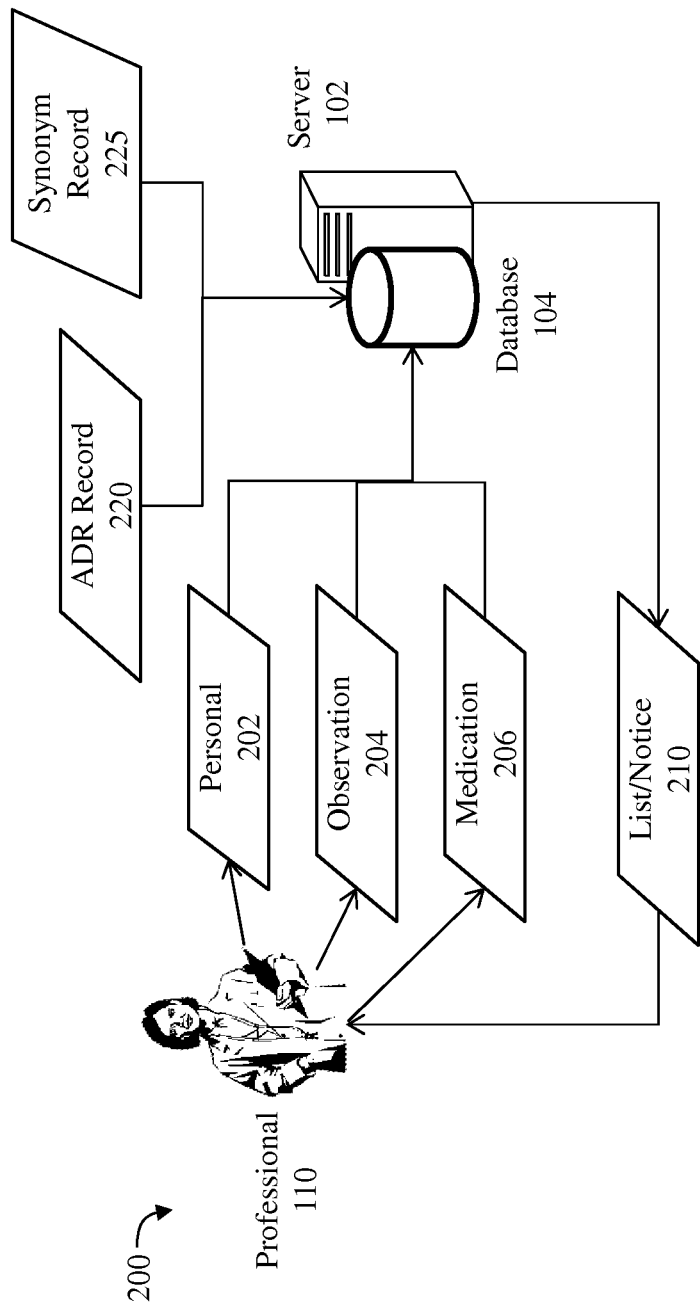
FIG. 2 is a diagram showing the data flow of the process for detection of ADR and storage and dissemination of related data, according to an example embodiment.

In one embodiment of the present invention, the server 102 may send data 304 to the communications server 130, wherein data 304 may include any of the data in the list 210 and notice of FIG. 2. The communications server 130 may send the patient 112, the professional 110, the doctor 302, or the insurance company 140 notices 306 (via telephone, text message, email, instant message, etc.) regarding the ADR experienced by the patient 112.

In step 418, the professional 110 or another healthcare professional, such as a doctor 302, charged with treating the patient 112 may decide to alter the medication regimen in response to the list 210, notice 302 or notice 306. If so, in step 420, the professional 110 or doctor 302 alters the medication regimen and communicates this fact to the patient 112. In one embodiment, the altered medication regimen is stored in conjunction with a patient record of the patient 112 in database 104.

Figure 5:
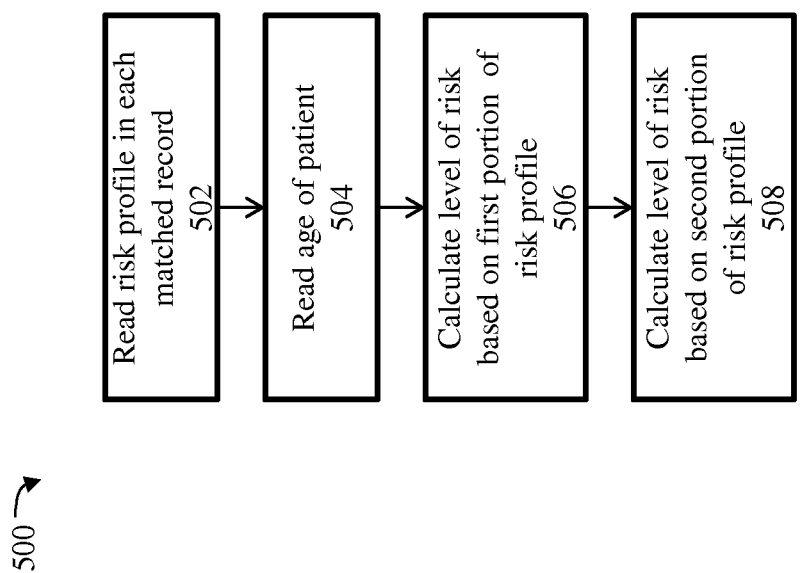
FIG. 5 is a flow chart providing more detail about the processes of calculating risk data, according to an example embodiment.

FIG. 5 is a flow chart of a method 500 for calculating risk data, according to an example embodiment. The method 500 provides more detail on the process performed by stage 410 of FIG. 4. Note that in stage 410, the server 102 calculates risk data for each of the ADR records matched in stage 408.

In a first step 502, the server 102 reads the risk profile in each of the matched ADR records of step 408. Recall that a risk profile may comprise more than one portion, wherein each portion may comprise a numerical probability, such as 50%, or may be a textual probability, such as acceptable risk, or high risk. The first portion of a risk profile may define a level of risk that the medication of the matched ADR record is causing the ADR description. The second portion of a risk profile may define a level of risk that the medication of the matched ADR record is causing the ADR description in a person of advanced age.

In step 504, the server 102 reads the age of the patient from the patient record or from data 202. In step 506, the server 102 deems a level of risk that the medication of the matched ADR record is causing the ADR description in data 204 to be equal to the first portion of the risk profile. In step 508, the server 102 deems a level of risk that the medication of the matched ADR record is causing the ADR description in data 204 to be equal to the second portion of the risk profile. In step 508, the server 102 provides both levels of risk to list 410 that describes each medication in each matched ADR record, and level of risk that the medication of each matched ADR record is causing the ADR description in data 204.

Figure 6:
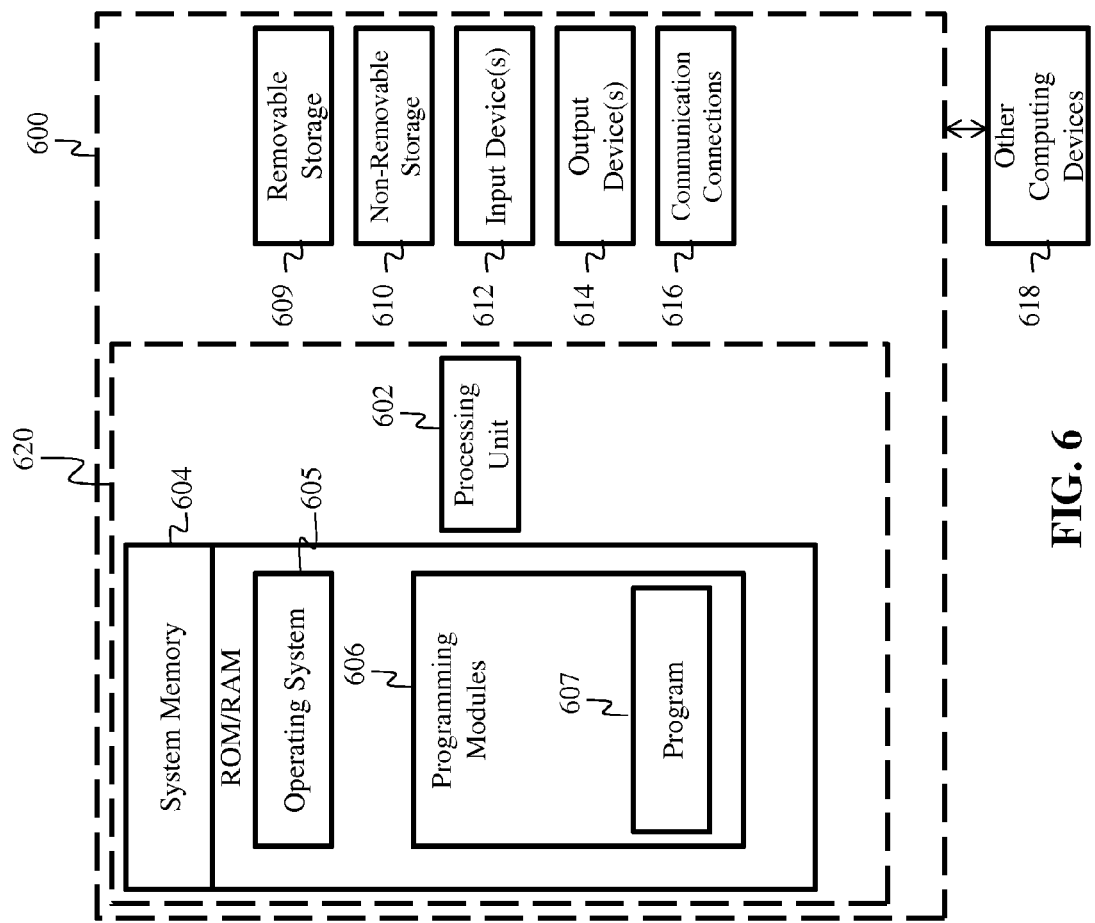
FIG. 6 is a block diagram of a system including a computing device, according to an example embodiment.

FIG. 6 is a block diagram of a system including an example computing device 600 and other computing devices. Consistent with the embodiments described herein, the aforementioned actions performed by servers 102, 130, and devices 120, 122 may be implemented in a computing device, such as the computing device 600 of FIG. 6. Any suitable combination of hardware, software, or firmware may be used to implement the computing device 600. The aforementioned system, device, and processors are examples and other systems, devices, and processors may comprise the aforementioned computing device. Furthermore, computing device 600 may comprise an operating environment for methods 400, 500 as described above. Methods 400, 500 may operate in other environments and is not limited to computing device 600.

With reference to FIG. 6, a system consistent with an embodiment of the invention may include a plurality of computing devices, such as computing device 600. In a basic configuration, computing device 600 may include at least one processing unit 602 and a system memory 604. Depending on the configuration and type of computing device, system memory 604 may comprise, but is not limited to, volatile (e.g. random access memory (RAM)), non-volatile (e.g. read-only memory (ROM)), flash memory, or any combination or memory. System memory 604 may include operating system 605, and one or more programming modules 606. Operating system 605, for example, may be suitable for controlling computing device 600's operation. In one embodiment, programming modules 606 may include, for example, a program module 607 for executing the actions of servers 102, 130, and devices 120, 122. Furthermore, embodiments of the invention may be practiced in conjunction with a graphics library, other operating systems, or any other application program and is not limited to any particular application or system. This basic configuration is illustrated in FIG. 6 by those components within a dashed line 620.

Computing device 600 may have additional features or functionality. For example, computing device 600 may also include additional data storage devices (removable and/or non-removable) such as, for example, magnetic disks, optical disks, or tape. Such additional storage is illustrated in FIG. 6 by a removable storage 609 and a non-removable storage 610. Computer storage media may include volatile and nonvolatile, removable and non-removable media implemented in any method or technology for storage of information, such as computer readable instructions, data structures, program modules, or other data. System memory 604, removable storage 609, and non-removable storage 610 are all computer storage media examples (i.e. memory storage.) Computer storage media may include, but is not limited to, RAM, ROM, electrically erasable read-only memory (EEPROM), flash memory or other memory technology, CD-ROM, digital versatile disks (DVD) or other optical storage, magnetic cassettes, magnetic tape, magnetic disk storage or other magnetic storage devices, or any other medium which can be used to store information and which can be accessed by computing device 600. Any such computer storage media may be part of device 600. Computing device 600 may also have input device(s) 612 such as a keyboard, a mouse, a pen, a sound input device, a camera, a touch input device, etc. Output device(s) 614 such as a display, speakers, a printer, etc. may also be included. The aforementioned devices are only examples, and other devices may be added or substituted.

Computing device 600 may also contain a communication connection 616 that may allow device 600 to communicate with other computing devices 618, such as over a network in a distributed computing environment, for example, an intranet or the Internet. Communication connection 616 is one example of communication media. Communication media may typically be embodied by computer readable instructions, data structures, program modules, or other data in a modulated data signal, such as a carrier wave or other transport mechanism, and includes any information delivery media. The term "modulated data signal" may describe a signal that has one or more characteristics set or changed in such a manner as to encode information in the signal. By way of example, and not limitation, communication media may include wired media such as a wired network or direct-wired connection, and wireless media such as acoustic, radio frequency (RF), infrared, and other wireless media. The term computer readable media as used herein may include both computer storage media and communication media.

As stated above, a number of program modules and data files may be stored in system memory 604, including operating system 605. While executing on processing unit 602, programming modules 606 (e.g. program module 607) may perform processes including, for example, one or more of method 400's or 500's stages as described above. The aforementioned processes are examples, and processing unit 602 may perform other processes. Other programming modules that may be used in accordance with embodiments of the present invention may include electronic mail and contacts applications, word processing applications, spreadsheet applications, database applications, slide presentation applications, drawing or computer-aided application programs, etc.

Generally, consistent with embodiments of the invention, program modules may include routines, programs, components, data structures, and other types of structures that may perform particular tasks or that may implement particular abstract data types. Moreover, embodiments of the invention may be practiced with other computer system configurations, including hand-held devices, multiprocessor systems, microprocessor-based or programmable consumer electronics, minicomputers, mainframe computers, and the like. Embodiments of the invention may also be practiced in distributed computing environments where tasks are performed by remote processing devices that are linked through a communications network. In a distributed computing environment, program modules may be located in both local and remote memory storage devices.

Furthermore, embodiments of the invention may be practiced in an electrical circuit comprising discrete electronic elements, packaged or integrated electronic chips containing logic gates, a circuit utilizing a microprocessor, or on a single chip (such as a System on Chip) containing electronic elements or microprocessors. Embodiments of the invention may also be practiced using other technologies capable of performing logical operations such as, for example, AND, OR, and NOT, including but not limited to mechanical, optical, fluidic, and quantum technologies. In addition, embodiments of the invention may be practiced within a general purpose computer or in any other circuits or systems.

Embodiments of the present invention, for example, are described above with reference to block diagrams and/or operational illustrations of methods, systems, and computer program products according to embodiments of the invention. The functions/acts noted in the blocks may occur out of the order as shown in any flowchart. For example, two blocks shown in succession may in fact be executed substantially concurrently or the blocks may sometimes be executed in the reverse order, depending upon the functionality/acts involved.

While certain embodiments of the invention have been described, other embodiments may exist. Furthermore, although embodiments of the present invention have been described as being associated with data stored in memory and other storage mediums, data can also be stored on or read from other types of computer-readable media, such as secondary storage devices, like hard disks, floppy disks, or a CD-ROM, or other forms of RAM or ROM. Further, the disclosed methods' stages may be modified in any manner, including by reordering stages and/or inserting or deleting stages, without departing from the invention.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

I claim:

1. A computer for detecting an adverse drug event in a patient via the use of a communications network, the computer comprising:
   a memory storage;
   a network connection device communicatively coupled with the communications network; and
   a processing device coupled to the memory storage, wherein the processing unit is operative for:
      receiving from a computing device, via the communications network, a plurality of adverse drug reaction (ADR) descriptions corresponding to the patient and a plurality of identifiers for medications that are currently taken by the patient, wherein the plurality of ADR descriptions and the plurality of identifiers for medications have been entered into a single graphical user interface by a user;
      accessing a plurality of ADR records corresponding to the plurality of identifiers for medications that are currently taken by the patient, wherein each record comprises an identifier for a medication, one or more ADR descriptions for the medication and a risk profile for the medication, wherein a risk profile comprises a numerical value in a continuous range from one to one hundred;
      comparing the plurality of ADR descriptions corresponding to the patient with ADR descriptions in the plurality of ADR records that were accessed;
      identifying at least one ADR record, of the plurality of ADR records that were accessed, which includes an ADR description matching at least one of the plurality of ADR descriptions corresponding to the patient;
      calculating a level of risk that at least one medication of the at least one ADR record is causing the matching ADR description corresponding to the patient, wherein the level of risk is calculated based on the risk profile in the at least one ADR record, and wherein a level of risk comprises a second numerical value in a continuous range from one to one hundred; and
      transmitting to the user, via the network connection device communicatively coupled with the communications network, an identifier for each medication of the at least one ADR record identified and a level of risk for each medication of the at least one ADR record, and a notice indicating that each medication of the at least one ADR record may be causing the matching ADR description corresponding to the patient.

2. The computer of claim 1, wherein the ADR description comprises alphanumeric text.

3. The computer of claim 2, wherein each of the plurality of identifiers for medications comprises alphanumeric text.

4. A computer for detecting an adverse drug event in a patient via the use of a communications network, the computer comprising:
   a memory storage;
   a network connection device communicatively coupled with the communications network; and
   a processing device coupled to the memory storage, wherein the processing unit is operative for:
      receiving from a computing device, via the communications network, a plurality of adverse drug reaction (ADR) descriptions corresponding to the patient and a plurality of identifiers for medications that are currently taken by the patient, wherein the plurality of ADR descriptions and the plurality of identifiers for medications have been entered into a single graphical user interface by a user;
      accessing a plurality of ADR records corresponding to the plurality of identifiers for medications that are currently taken by the patient, wherein each record comprises an identifier for a medication, one or more ADR descriptions for the medication and, for each ADR description, a risk profile for the medication, wherein a risk profile comprises a first portion defining a level of risk that the medication of the ADR record is causing the ADR description, and a second portion defining a level of risk that the medication of the ADR record is causing the ADR description in an elderly patient, wherein an elderly patient is defined as a person over sixty five years of age, and wherein both the first portion and the second portion each comprise a numerical value in a continuous range from one to one hundred;
      comparing the plurality of ADR descriptions corresponding to the patient with ADR descriptions in the plurality of ADR records that were accessed;
      identifying at least one ADR record, of the plurality of ADR records that were accessed, which includes an ADR description matching at least one of the plurality of ADR descriptions corresponding to the patient;
      calculating two levels of risk for each medication of the at least one ADR record, wherein the first level of risk indicates a probability that a medication is causing the matching ADR description corresponding to the patient, wherein the second level of risk indicates a probability that a medication is causing the matching ADR description corresponding to an elderly patient, wherein the first and second levels of risk are calculated based on the risk profile in the at least one ADR record, and wherein the first and second levels of risk each comprise a second and a third numerical value in a continuous range from one to one hundred; and
      transmitting to the user, via the network connection device communicatively coupled with the communications network, an identifier for each medication of the at least one ADR record identified, the two levels of risk for each medication in the at least one ADR record, and a notice indicating that each medication of the at least one ADR record may be causing the matching ADR description corresponding to the patient.

5. A computer for detecting an adverse drug event in a patient via the use of a communications network, the computer comprising:
   a memory storage;
   a network connection device communicatively coupled with the communications network; and
   a processing device coupled to the memory storage, wherein the processing unit is operative for:
      receiving from a computing device, via the communications network, a plurality of adverse drug reaction (ADR) descriptions corresponding to the patient and a plurality of identifiers for medications that are currently taken by the patient, wherein the plurality of ADR descriptions and the plurality of identifiers for medications have been entered into a single graphical user interface by a user;
      accessing a plurality of synonym records corresponding to the plurality of identifiers for medications that are currently taken by the patient, wherein each synonym record comprises alphanumeric text corresponding to synonyms describing the ADR description;
      comparing the plurality of ADR descriptions corresponding to the patient with alphanumeric text in the plurality of synonym records that were accessed;

identifying at least one synonym record, of the plurality of synonym records that were accessed, which includes alphanumeric text matching at least one of the plurality of synonym records for the ADR description corresponding to the patient;

accessing a plurality of ADR records corresponding to the at least one synonym record, wherein each ADR record comprises an identifier for a medication, one or more ADR descriptions for a medication and a risk profile for the medication, wherein a risk profile comprises a numerical value in a continuous range from one to one hundred;

calculating a level of risk that at least one medication of the one or more ADR records is causing the matching ADR description corresponding to the patient, wherein the level of risk is calculated based on the risk profile in the one or more ADR records, and wherein a level of risk comprises a numerical value in a continuous range from one to one hundred; and transmitting to the user, via the network connection device communicatively coupled with the communications network, an identifier for each medication of the at least one ADR record identified and a level of risk for each medication of the one or more ADR records, and a notice indicating that each medication of the one or more ADR records may be causing the matching ADR description corresponding to the patient.

* * * * *